United States Patent
Lin et al.

(10) Patent No.: US 10,980,399 B2
(45) Date of Patent: Apr. 20, 2021

(54) MEDICAL INSTRUMENT

(71) Applicant: HIWIN TECHNOLOGIES CORP., Taichung (TW)

(72) Inventors: Wei-Lun Lin, Taichung (TW); Zong-Sian Jiang, Taichung (TW); Hung-Chuan Hsu, Taichung (TW); Yu-Lin Chu, Taichung (TW)

(73) Assignee: HIWIN TECHNOLOGIESCORP., Taichung (TW)

( * ) Notice: Subject to any disclaimer, the term of this patent is extended or adjusted under 35 U.S.C. 154(b) by 667 days.

(21) Appl. No.: 15/818,865

(22) Filed: Nov. 21, 2017

(65) Prior Publication Data

US 2019/0150712 A1 May 23, 2019

(51) Int. Cl.
| | | |
|---|---|---|
| *A61B 1/00* | (2006.01) | |
| *A61B 1/04* | (2006.01) | |
| *A61B 17/29* | (2006.01) | |
| *A61B 34/20* | (2016.01) | |
| *A61B 34/30* | (2016.01) | |

(Continued)

(52) U.S. Cl.
CPC ...... *A61B 1/00087* (2013.01); *A61B 1/00009* (2013.01); *A61B 1/00149* (2013.01); *A61B 1/04* (2013.01); *A61B 17/29* (2013.01); *A61B 17/00234* (2013.01); *A61B 2017/00907* (2013.01); *A61B 2017/2901* (2013.01); *A61B 2017/2903* (2013.01); *A61B 2017/2937* (2013.01); *A61B 2034/2065* (2016.02);

(Continued)

(58) Field of Classification Search
None
See application file for complete search history.

(56) References Cited

U.S. PATENT DOCUMENTS

2004/0006333 A1   1/2004  Arnold et al.
2008/0004603 A1 * 1/2008  Larkin .................. A61B 34/20
                                                               606/1

(Continued)

FOREIGN PATENT DOCUMENTS

| DE | 102007053398 A1 | 5/2008 |
| DE | 102014101455 A1 | 8/2015 |
| JP | H0928713 A | 2/1997 |

OTHER PUBLICATIONS

Machine Translated English Version JPH 0928713A Hiroyuki, 1997.*

(Continued)

*Primary Examiner* — Michael J Carey
*Assistant Examiner* — Minqiao Huang
(74) *Attorney, Agent, or Firm* — Burris Law, PLLC

(57) ABSTRACT

A medical instrument includes an instrument body and an operating mechanism. The instrument body has a window portion having a light permeable segment. The operating mechanism includes an indicator unit and an operating unit. The indicator unit is disposed in the window portion, and is changeable between a detectable state where the indicator unit is detectable through the light permeable segment of the window portion and a non-detectable state where the indicator unit is non-detectable through the light permeable segment. The operating unit is connected to the indicator unit and operable to change the indicator unit between the detectable and non-detectable states. An endoscopy system including the medical instrument is also disclosed.

4 Claims, 15 Drawing Sheets

(51) Int. Cl.
 *A61B 90/00* (2016.01)
 *A61B 17/00* (2006.01)
(52) U.S. Cl.
 CPC . *A61B 2034/301* (2016.02); *A61B 2090/0811* (2016.02); *A61B 2090/3937* (2016.02)

(56) References Cited

U.S. PATENT DOCUMENTS

| | | | | |
|---|---|---|---|---|
| 2009/0287227 | A1* | 11/2009 | Newell | A61B 17/0401 606/148 |
| 2011/0130773 | A1* | 6/2011 | Saliman | A61B 17/0482 606/145 |
| 2013/0123921 | A1* | 5/2013 | Jones | A61B 17/88 623/16.11 |
| 2016/0074101 | A1* | 3/2016 | Anglese | A61B 18/1447 606/47 |
| 2016/0235486 | A1* | 8/2016 | Larkin | A61B 1/00154 |
| 2017/0014136 | A1* | 1/2017 | Martin | A61B 17/1227 |
| 2019/0314011 | A1* | 10/2019 | Aravalli | A61B 34/30 |

OTHER PUBLICATIONS

Search Report appended to an Office Action issed to Taiwanese counterpart application No. 106125728 by the TIPO dated May 1, 2018, with an English translation thereof.

\* cited by examiner

MEDICAL INSTRUMENT

FIELD

The disclosure relates to a medical instrument, and more particularly to a medical instrument including an indicator unit that is operable to change between a detectable state and a non-detectable state, and to an endoscopy system including the medical instrument.

BACKGROUND

A conventional endoscopy system, as disclosed in Taiwanese Patent No. 1517828, includes a processing unit, an image capture unit, an endoscope unit, and two medical instruments each having a color ring. An image of the two medical instruments captured by the image capture unit is analyzed by the processing unit, and the processing unit drives the image capture unit to move to a position such that a center of the image captured by the image capture unit is located at a midpoint between the color rings of the two medical instruments. However, the medical instruments are manually and frequently moved toward or away from each other during a surgical operation, such moving action may result in unexpected and undesired movement of the endoscope unit and the image captured may not be stable, which may distract an operator and adversely affect the surgical operation.

SUMMARY

Therefore, an object of the disclosure is to provide a medical instrument that can alleviate at least one of the drawbacks of the prior art.

According to one aspect of the disclosure, the medical instrument includes an instrument body and an operating mechanism.

The instrument body has a hand-held portion, a surgical tool portion that is opposite to the hand-held portion, and a hollow window portion that interconnects the hand-held portion and the surgical tool portion, and that has a light impermeable segment and a light permeable segment being adjacent to the light impermeable segment. The operating mechanism includes an operating unit that is operably disposed on the hand-held portion of the instrument body, a transmission unit that is disposed in the window portion of the instrument body and that is connected to and movably driven by the operating unit, and a marker that is connected to the transmission unit and that is movable together with the transmission unit within the window portion of the instrument body between a non-detectable state, where the marker is placed within the light impermeable segment, and a detectable state, where the marker is placed within the light permeable segment. According to another aspect of the disclosure, the medical instrument for use in endoscopy includes an instrument body and an operating mechanism.

The instrument body has a hand-held portion, a surgical tool portion that is opposite to the hand-held portion, and a hollow window portion that interconnects the hand-held portion and the surgical tool portion, and that has a light permeable segment. The operating mechanism includes an indicator unit and an operating unit. The indicator unit is disposed in the window portion of the instrument body, and is changeable between a detectable state where the indicator unit is detectable through the light permeable segment of the window portion and a non-detectable state where the indicator unit is non-detectable through the light permeable segment. The operating unit is disposed on the hand-held portion of the instrument body and is connected to the indicator unit. The operating unit is operable to change the indicator unit between the detectable and non-detectable states.

According to yet another aspect of the disclosure, an endoscopy system includes the above-mentioned medical instrument, an endoscope unit, a mechanical arm unit, an image analysis module, and a control unit.

The endoscope unit is disposed to capture image of the medical instrument. The mechanical arm unit is connected to the endoscope unit for driving movement of the endoscope unit. The image analysis module is electrically communicated with the endoscope unit to generate a control signal when the image captured by the endoscope unit shows that the indicator unit is in the detectable state. The control unit is electrically communicated with the endoscope unit, the image analysis module, and the mechanical arm unit, and operable to actuate the mechanical arm unit to drive movement of the endoscope unit or to actuate said endoscope unit to change focus upon receipt of the control signal.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
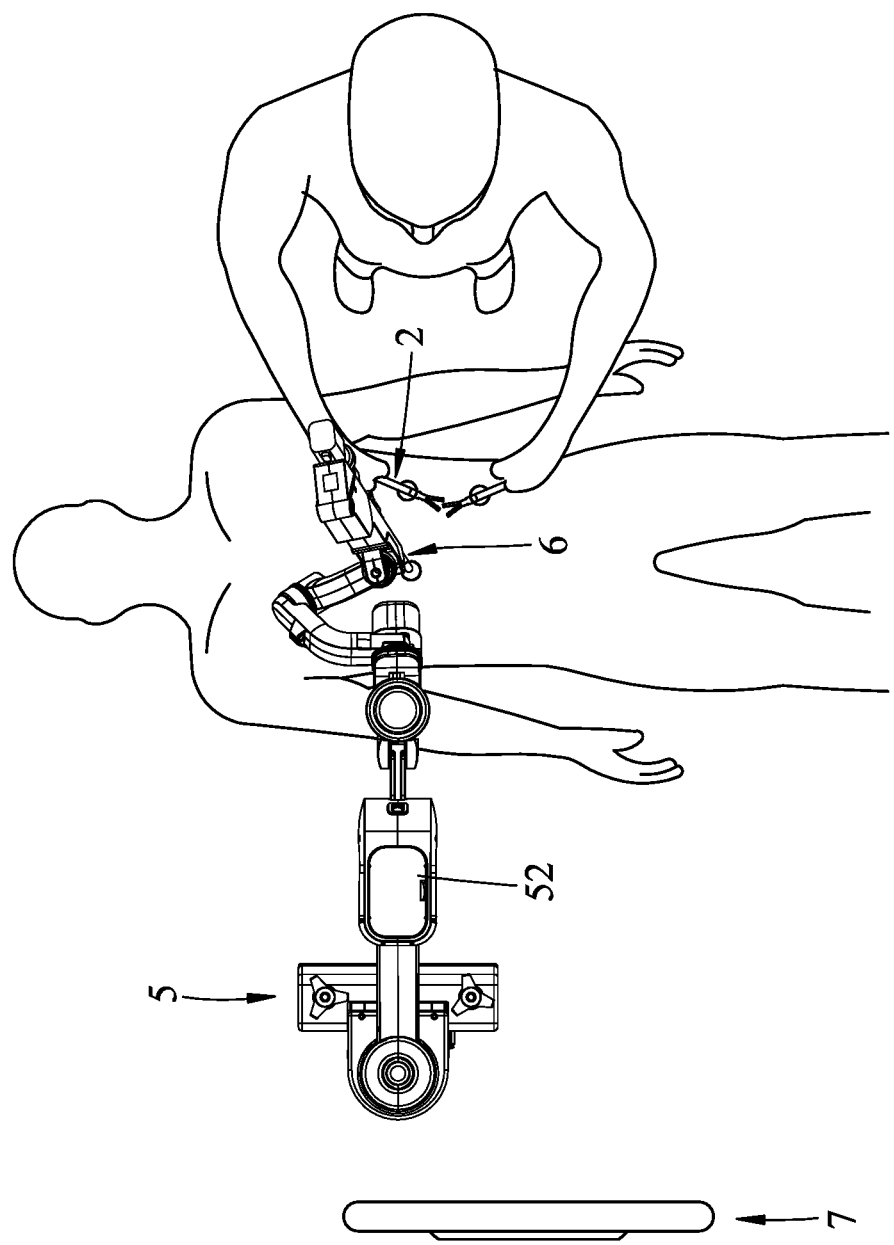
FIG. 1 is a schematic perspective view illustrating a first embodiment of an endoscopy system according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
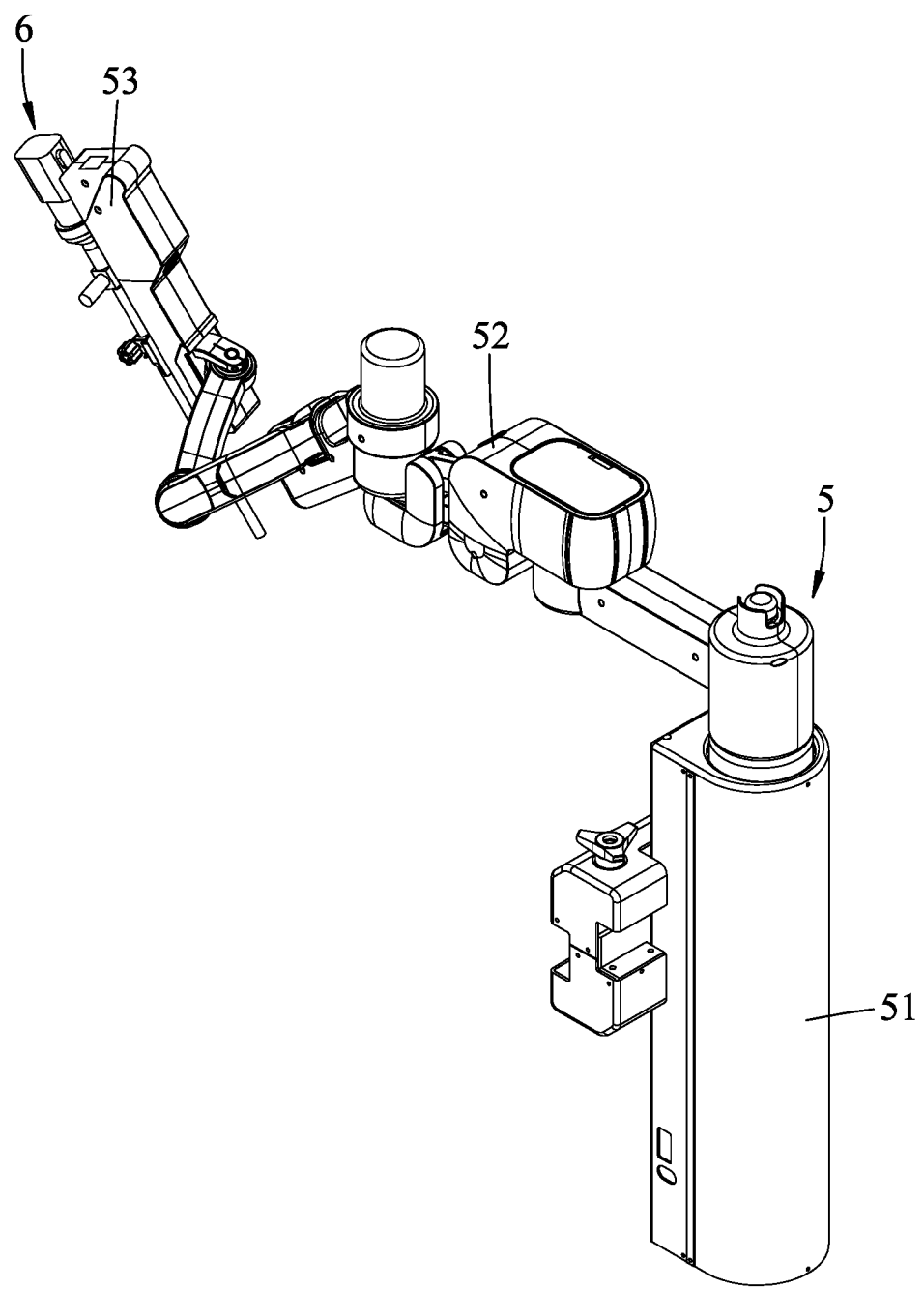
FIG. 2 is a perspective view illustrating a mechanical arm unit of the first embodiment.
Figure 3:
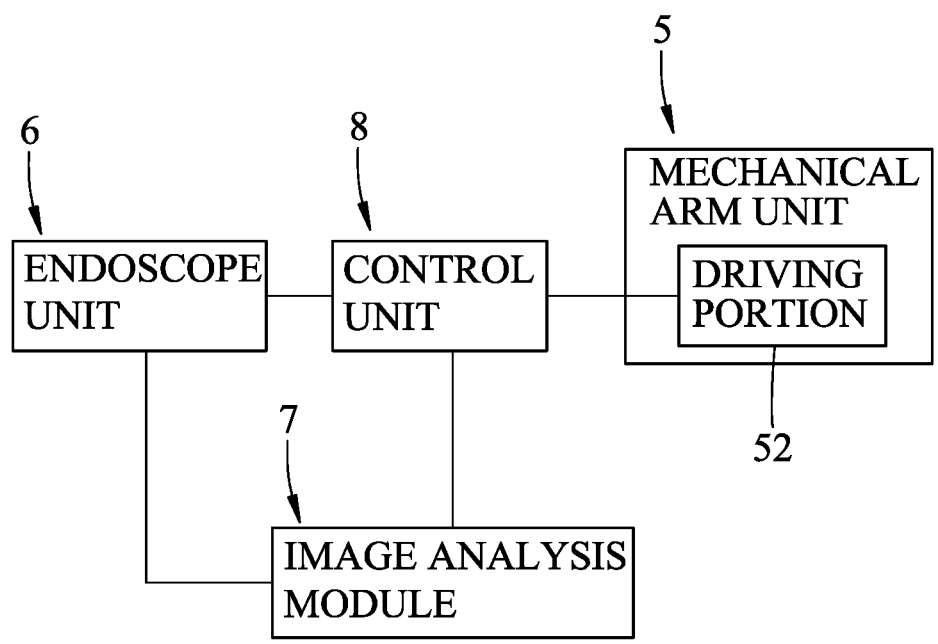
FIG. 3 is a circuit block diagram of the first embodiment.
Figure 4:
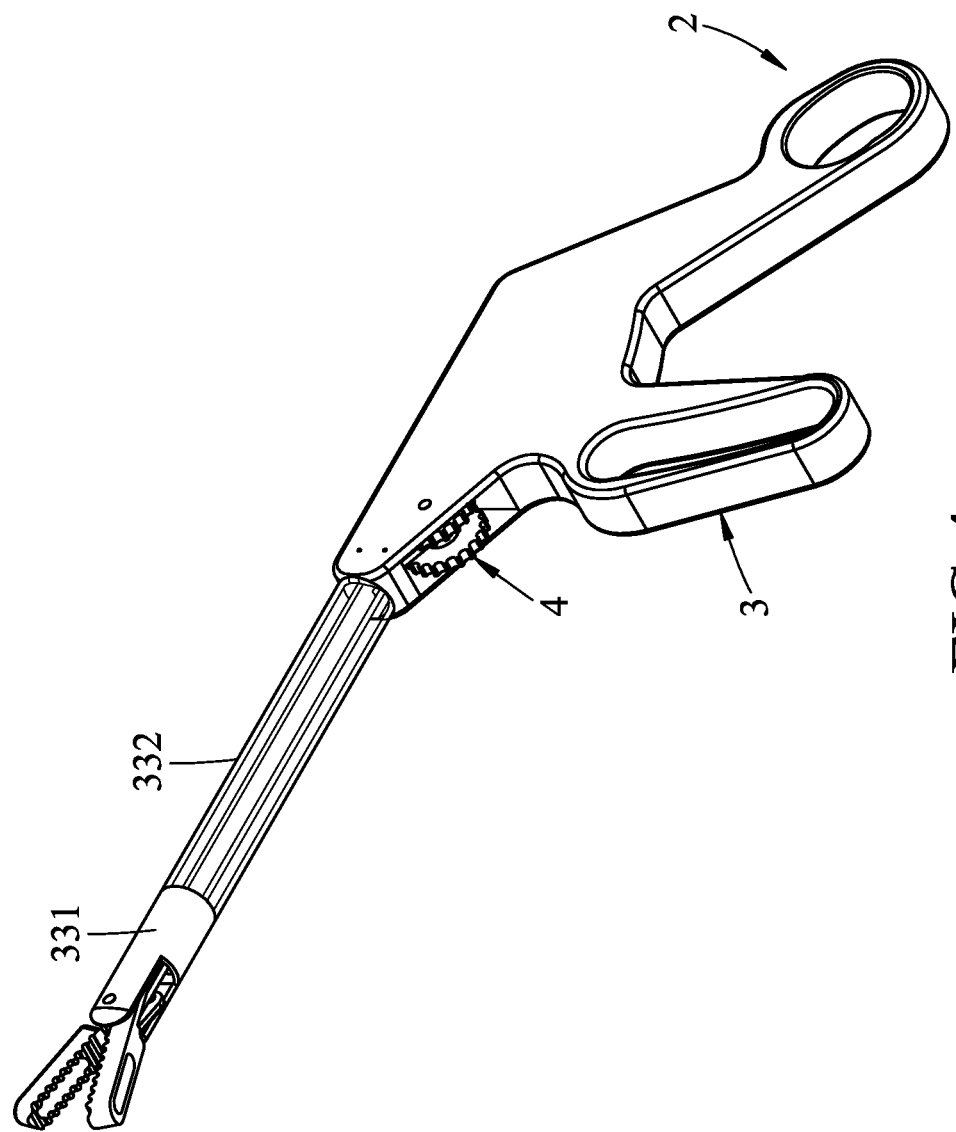
FIG. 4 is a perspective view of a medical instrument of the first embodiment having an indicator unit in a non-detectable state.
Figure 5:
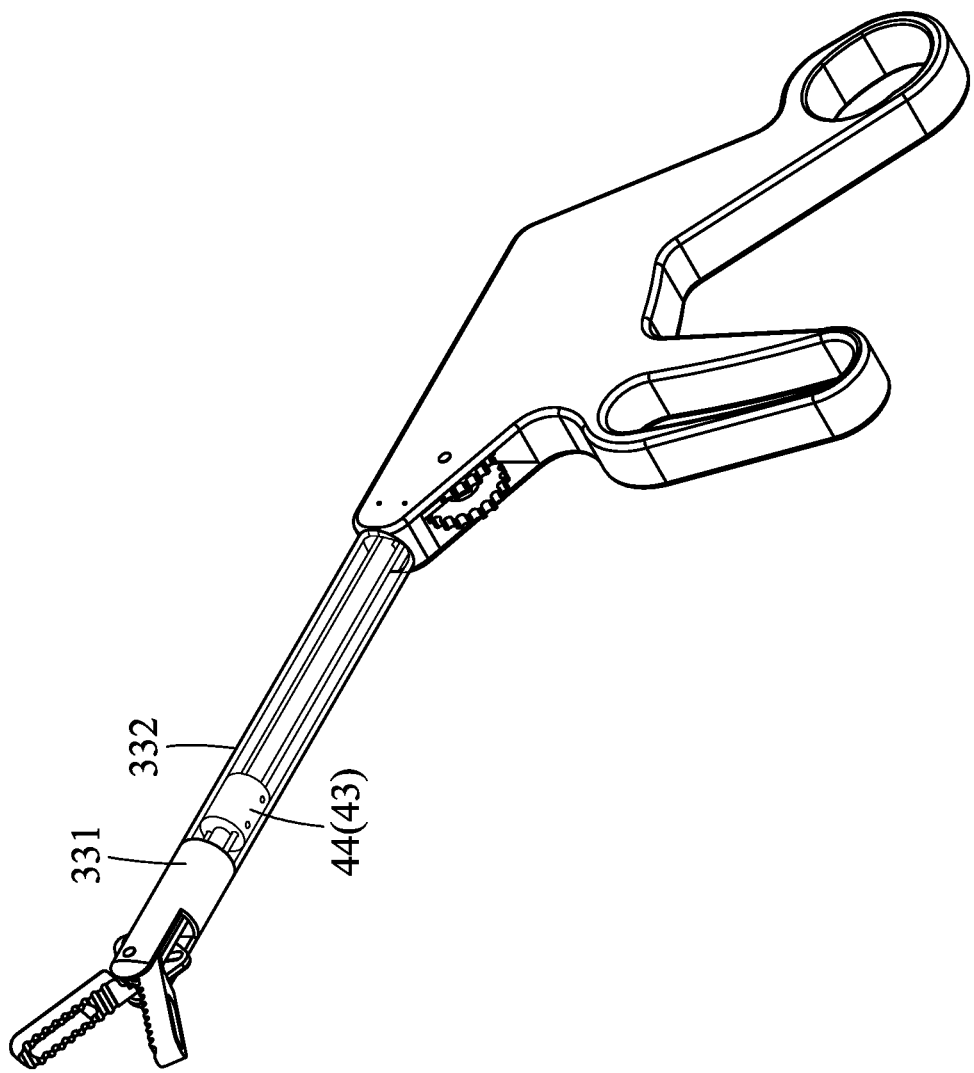
FIG. 5 is a view similar to FIG. 4, but illustrating the indicator unit in a detectable state.
Figure 6:
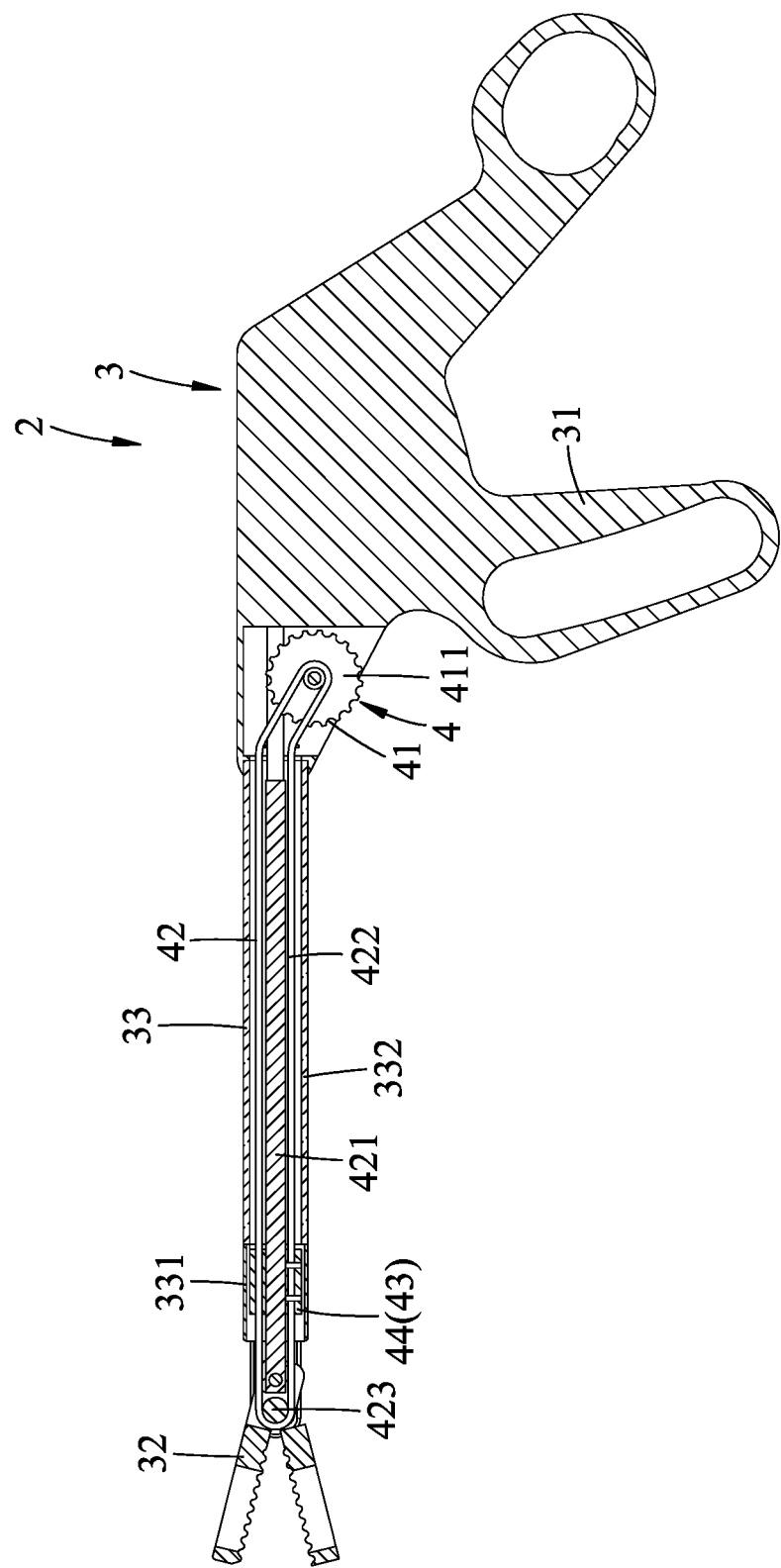
FIG. 6 is a sectional view of the medical instrument of the first embodiment, illustrating the indicator unit in the non-detectable state.
Figure 7:
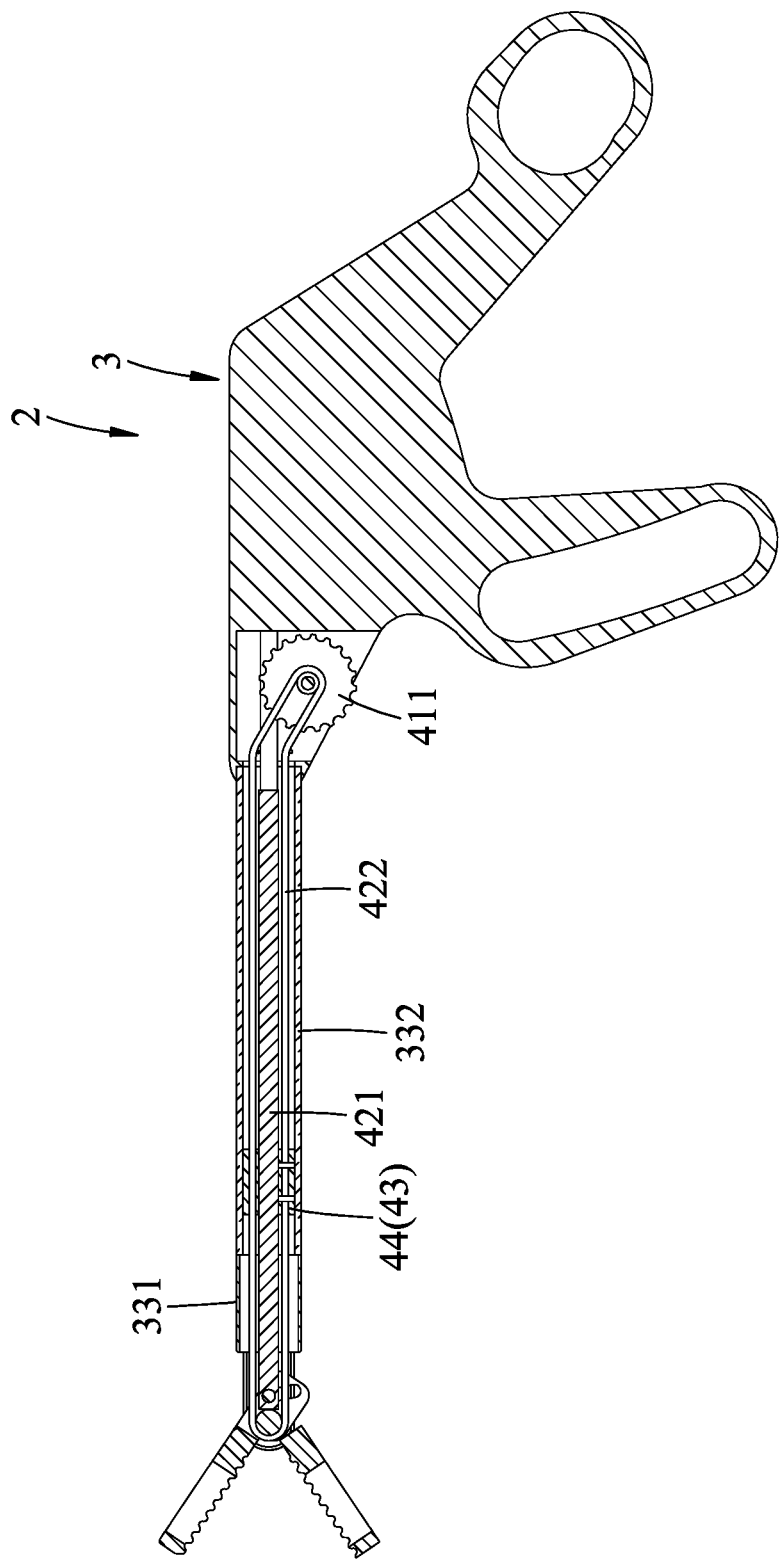
FIG. 7 is a view similar to FIG. 6, but illustrating the indicator unit in the detectable state.

Referring to FIGS. 1 to 3, an embodiment of an endoscopy system includes a medical instrument 2, an endoscope unit 6, a mechanical arm unit 5, an image analysis module 7, and a control unit 8.

Referring to FIGS. 4 to 7, the medical instrument includes an instrument body 3 and an operating mechanism 4.

The instrument body 3 has a hand-held portion 31, a surgical tool portion 32 that is opposite to the hand-held portion 31, and a hollow window portion 33 that interconnects the hand-held portion 31 and the surgical tool portion 32, and that has a light permeable segment 332. In this embodiment, the window portion 33 is tubular in shape, and the surgical tool portion 32 is, but not limited to be, a surgical clamp.

The operating mechanism 4 includes an indicator unit 44 and an operating unit 41. The indicator unit 44 is disposed in the window portion 33 of the instrument body 3, and is changeable between a detectable state (see FIGS. 5 and 7) where the indicator unit 44 is detectable through the light permeable segment 332 of the window portion 33, and a non-detectable state (see FIGS. 4 and 6) where the indicator unit 44 is non-detectable through the light permeable segment 332. The operating unit 41 is operably disposed on the hand-held portion 31 of the instrument body 3 and is connected to the indicator unit 44. The operating unit 41 is operable to change the indicator unit 44 between the detectable and non-detectable states.

In this embodiment, the window portion 33 of the instrument body 3 further has a light impermeable segment 331 being adjacent to the light permeable segment 332, and the light permeable segment 332 is made of a transparent material. The indicator unit 44 has a marker 43 which is a movable solid piece disposed within the window portion 33, and which is movable within the window portion 33 from the light impermeable segment 331 to the light permeable segment 332 and vice versa.

The operating unit 41 of this embodiment includes a wheel piece 411 rotatably disposed in the hand-held portion 31 of the instrument body 3, and the operating mechanism 4 further includes a transmission unit 42 that is disposed in the window portion 33 of the instrument body 3, that is connected to and movably driven by the operating unit 41, and that includes a shaft 421, a pulley 423, and a cord 422.

The shaft 421 is disposed between the hand-held portion 31 and the surgical tool portion 32 of the instrument body 3 and within the window portion 33 of the instrument body 3, and extends through the marker 43.

The pulley 423 is disposed within the window portion 33 at an end of the shaft 421 which is distal from the wheel piece 411 (i.e., proximal to the surgical tool portion 32). That is, the shaft 421 has one end proximal to the pulley 423 and the other end proximal to the wheel piece 411.

The cord 422 is wound around the pulley 423 and the wheel piece 411, extends at two opposite sides of and along the shaft 421, and threads through the marker 43 at the two opposite sides of the shaft 421. More specifically, the marker 43 is slidable along the shaft 421 and is fixed to a part of the cord 422, and has a color different from that of the light impermeable segment 331. In this way, the cord 422 can be driven by the wheel piece 411 to move the marker 43 between the detectable state, where the marker 43 is placed within the light permeable segment 332, and the non-detectable state, where the marker 43 is placed within the light impermeable segment 331.

Referring back to FIGS. 1 to 3, the endoscope unit 6 is disposed to capture image of the medical instrument 2.

The mechanical arm unit 5 is connected to the endoscope unit 6 for driving movement of the endoscope unit 6. The mechanical arm unit 5 has a base portion 51, a holding portion 53 that holds the endoscope unit 6, and a driving portion 52 that interconnects the base portion 51 and the holding portion 53, and that is actuated by the control unit 8 for driving movement of the endoscope unit 6.

The image analysis module 7 is electrically communicated with the endoscope unit 6 to generate a control signal when the image captured by the endoscope unit 6 shows that the indicator unit 44 is in the detectable state. It should be noted that the control signal may vary based on actual practice. The control signal may be for driving a center of the image captured by the endoscope unit 6 to be at a predetermined location, for changing the focus of the endoscope unit 6, or for driving movement of other mechanical arm unit 5 (not shown) which is used together with the mechanical arm unit 5 of this embodiment, and is not limited thereto.

The control unit 8 is electrically communicated with the endoscope unit 6, the image analysis module 7, and the mechanical arm unit 5 and is operable to actuate the mechanical arm unit 5 to drive movement of the endoscope unit 6 upon receipt of the control signal, or to actuate the endoscope unit 6 to zoom in or zoom out, for example.

Figure 8:
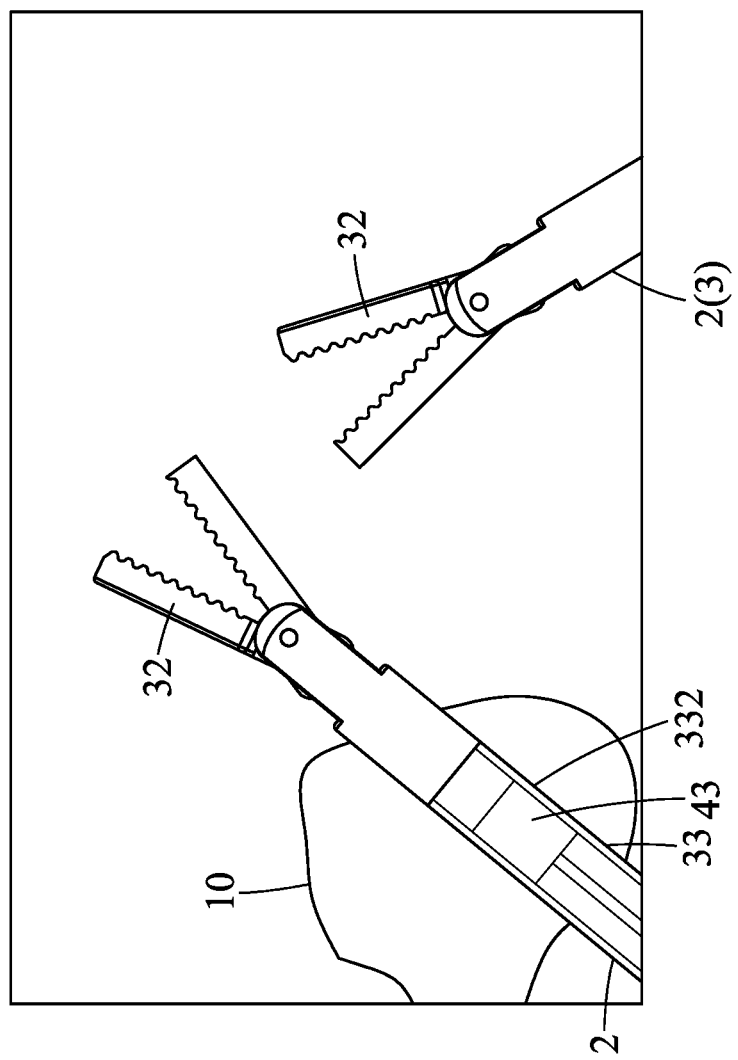
FIG. 8 is a schematic view illustrating an image captured by an endoscope unit of the first embodiment with the indicator unit in the detectable state.

When in use, an operator can rotate the wheel piece 411 to move the cord 422, so that the marker 43 can slide along the shaft 421 and change between the detectable and non-detectable states. The image captured by the endoscope unit 6 is used as an aid when performing a surgical operation using the medical instrument 2. Therefore, when it is desired to move the endoscope unit 6 to a different position for changing a view of the image captured by the endoscope unit 6, the wheel piece 411 can be rotated to slide the marker 43 to the detectable state, such that the marker 43 can be shown in the image (see FIG. 8). At this time, the image analysis module 7 generates a control signal upon recognition of the marker 43 in the image to actuate the driving portion 52 of the mechanical arm unit 5 to move the endoscope unit 6 to a proper position, such that a center of the image captured by the endoscope unit 6 is at a predetermined location, such as at a center of an anatomical site 10 where the surgical operation is to be performed (see FIG. 9).

It is worth noting that the predetermined location may be set to be a center of the marker 43, a location away from the marker 43 by a fixed distance, or other desired location according to actual needs.

Figure 9:
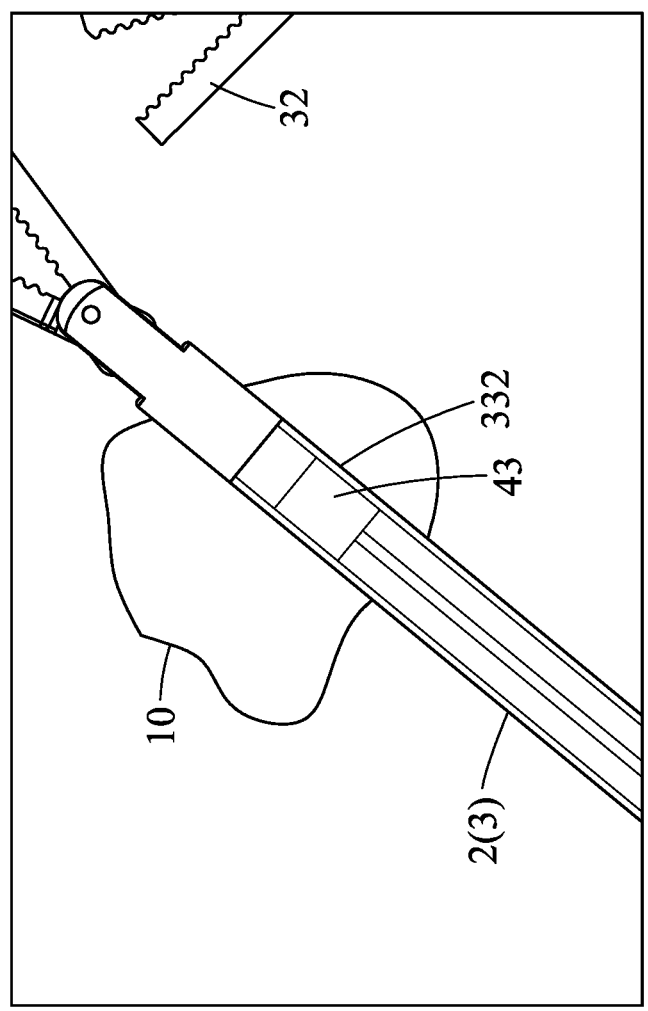
FIG. 9 is another schematic view illustrating an image captured by the endoscope unit with the indicator unit moved to a center of the image.

When the predetermined location is reached, as shown in FIG. 9, the indicator unit 44 can be operated to change to the non-detectable state by rotating the wheel piece 411. In the non-detectable state, the control unit 8 no longer actuates movement of the mechanical arm unit 5, and unexpected or undesired movement of the endoscope unit 6 is effectively prevented.

Figure 10:
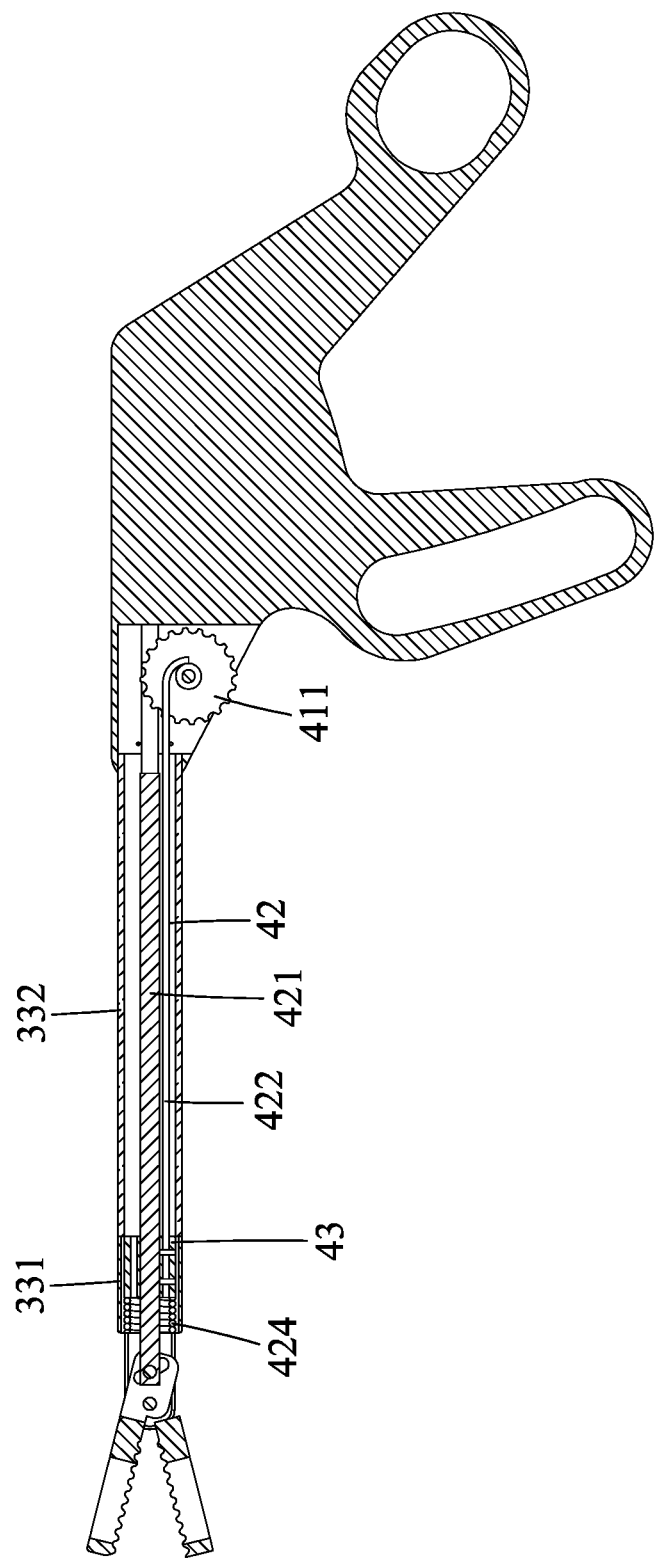
FIG. 10 is a sectional view of the medical instrument of a second embodiment of the endoscopy system according to the disclosure, illustrating the indicator unit in the non-detectable state.
Figure 11:
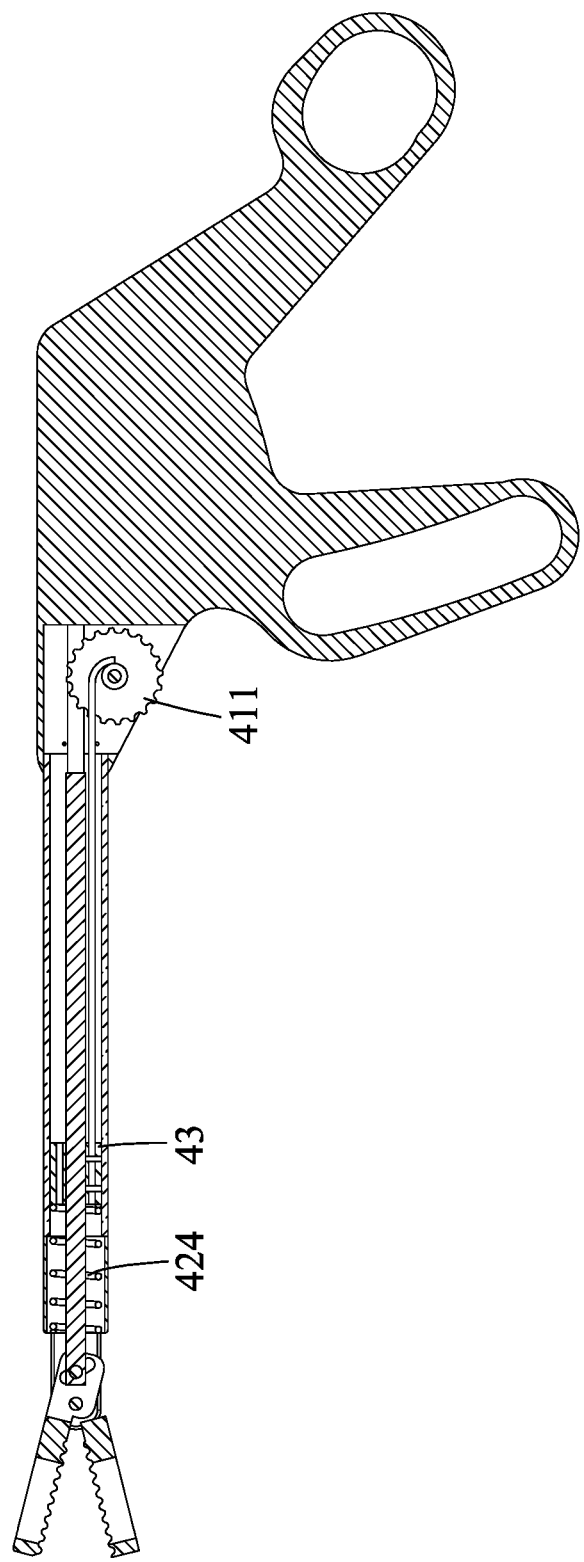
FIG. 11 is a view similar to FIG. 10, but illustrating the indicator unit in the detectable state.

FIGS. 10 and 11 illustrate a second embodiment of the endoscopy system according to the disclosure, in which the transmission unit 42 of the operating mechanism 4 of the medical instrument 2 further includes a resilient member 424 disposed on the shaft 421 and connected to the marker 43, and biasing the marker 43 to move to the non-detectable state. The wheel piece 411 can be rotated by an operator against a biasing force of the resilient member 424 to move the indicator unit 44 to the detectable state. Due to the biasing force of the resilient member 424, the indicator unit 44 can automatically move back to the non-detectable state upon releasing contact of the operator's hand on the wheel piece 411.

Figure 12:
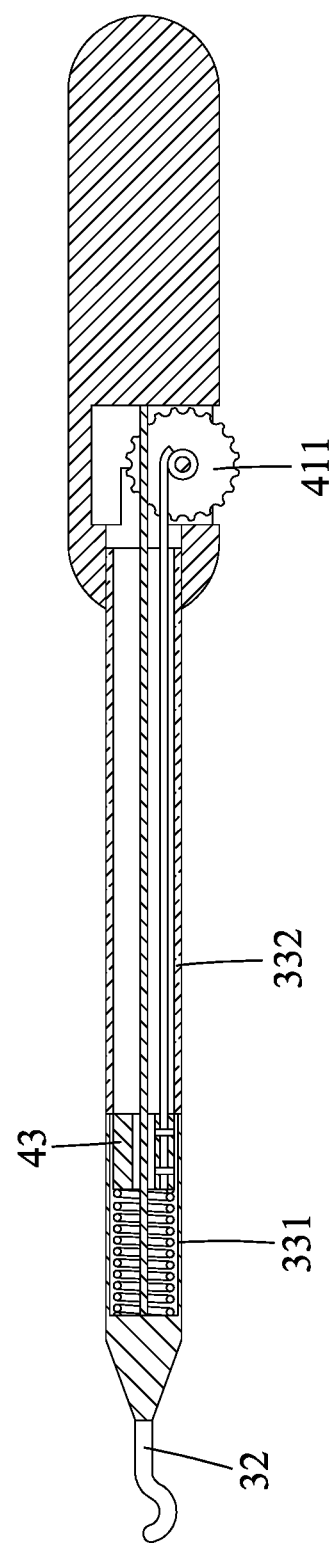
FIG. 12 is a sectional view of the medical instrument of a third embodiment of the endoscopy system according to the disclosure, illustrating the indicator unit in the non-detectable state.
Figure 13:
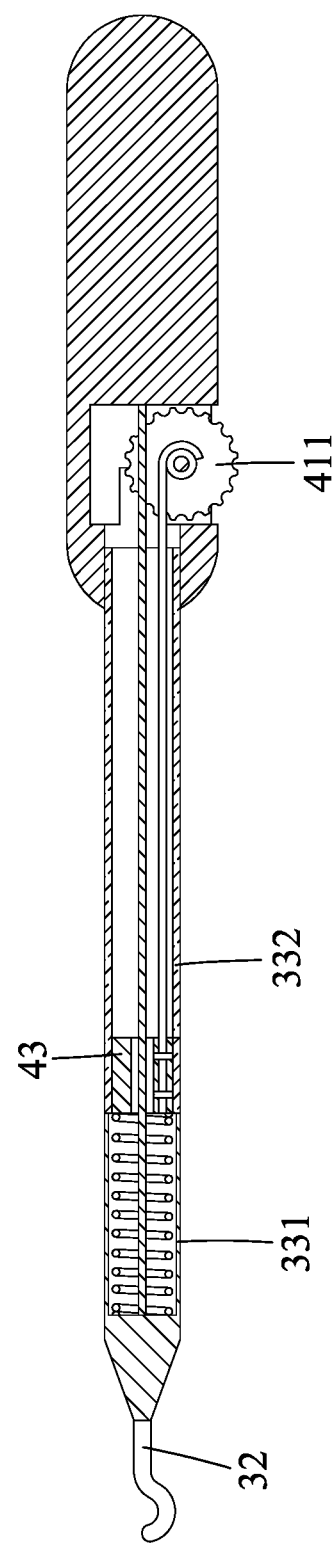
FIG. 13 is a view similar to FIG. 12, but illustrating the indicator unit in the detectable state.

It should be noted that, in other embodiments, the surgical tool portion 32 of the instrument body 3 of the medical instrument 2 may be other types of surgical tools. FIGS. 12 and 13 illustrate a third embodiment of the endoscopy system according to the disclosure which is structurally similar to the second embodiment, and in which the surgical tool portion 32 of the instrument body 3 is an electric knife.

Figure 14:
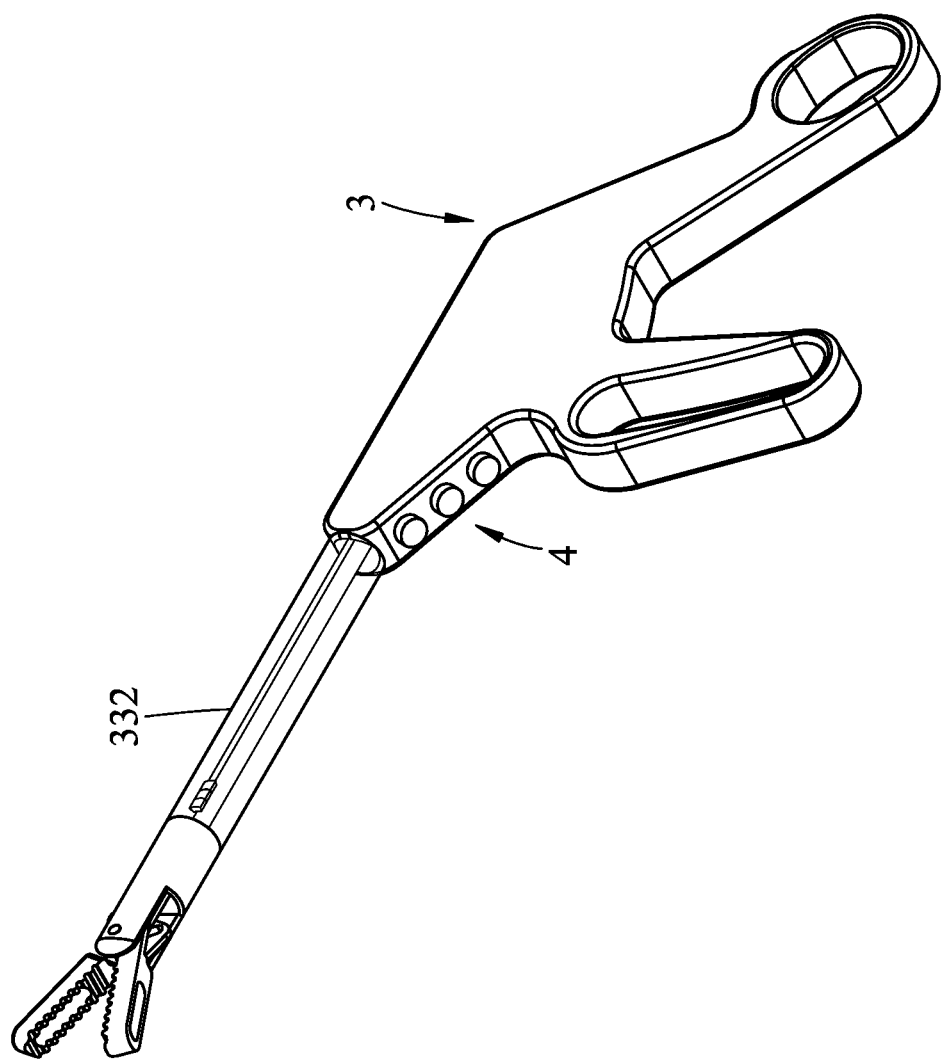
FIG. 14 is a perspective view of the medical instrument of a fourth embodiment of the endoscopy system according to the disclosure.
Figure 15:
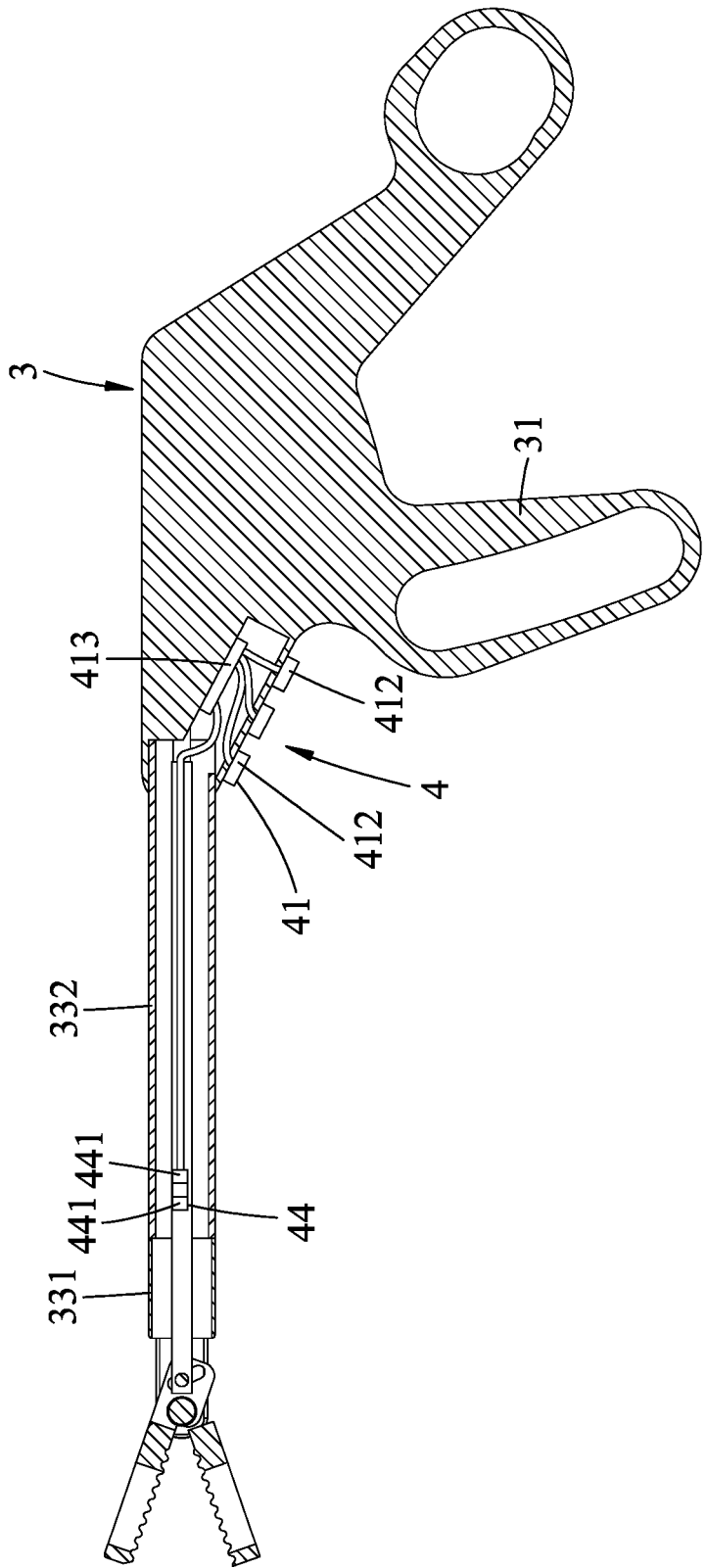
FIG. 15 is a sectional view of the medical instrument of the fourth embodiment.

FIGS. 14 and 15 illustrate a fourth embodiment of the endoscopy system, which differs from the first embodiment in the structure of the operating mechanism 4. The indicator unit 44 of this embodiment has three indicator lights 441, and the operating unit 41 includes a circuit board 413 in electrical communication with the indicator lights 441, and three control buttons 412 in electrical communication with the circuit board 413 and the indicator lights 441, and operable for controlling on and off of the indicator lights 441, respectively. The indicator lights 441 are on in the detectable state, and are off in the non-detectable state.

When one of the indicator lights 441 is on, the image analysis module 7 generates the control signal for driving movement of the endoscope unit 6. In this embodiment, each of the indicator lights 441 corresponds to a different setting, such as moving the center of the image to a center point of the indicator unit 44, zooming in or out of the image, etc. Alternatively, the indicator unit 44 may have only one indicator light 441.

In summary, by virtue of the configuration of the operating mechanism 4, the indicator unit 44 is changeable between the detectable and non-detectable states, so that the image captured by the image analysis module 7 can remain stable during a surgical operation. Furthermore, the operating unit 41 can be operated single-handedly, thereby enhancing convenience in use during the surgical operation.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A medical instrument comprising: an instrument body having a hand-held portion, a surgical tool portion that is opposite to said hand-held portion, and a hollow window portion that interconnects said hand-held portion and said surgical tool portion, and that has a light impermeable segment and a light permeable segment being adjacent to said light impermeable segment; and an operating mechanism including an operating unit that is operably disposed on said hand-held portion of said instrument body, a transmission unit that is disposed in said window portion of said instrument body and that is connected to and movably driven by said operating unit, and a marker that is connected to said transmission unit and that is movable together with said transmission unit within said window portion of said instrument body between a non-detectable state, where said marker is placed within said light impermeable segment, and a detectable state, where said marker is placed within said light permeable segment;

wherein said marker has a color different from that of said light impermeable segment;

wherein: said operating unit includes a wheel piece rotatably disposed in said hand-held portion of said instrument body; and said transmission unit includes a shaft disposed between said hand-held portion and said surgical tool portion of said instrument body and within said window portion of said instrument body, and extending through said marker, and a cord coupled to said marker, and connected to and driven by said wheel piece to move said marker between the detectable and non-detectable states.

2. The medical instrument as claimed in claim 1, wherein: said transmission unit of said operating mechanism further includes a pulley disposed at an end of said shaft which is distal from said wheel piece; and said cord is wound around said pulley and said wheel piece.

3. The medical instrument as claimed in claim 1, wherein: said transmission unit of said operating mechanism further includes a pulley disposed within said window portion proximal to said surgical tool portion; said marker is a movable solid piece disposed within said window portion; said shaft has one end proximal to said pulley and the other end proximal to said wheel piece, and extends through said movable solid piece; said cord is wound around said pulley and said wheel piece, extends at two opposite sides of and along said shaft, and threads through said movable solid piece at said two opposite sides of said shaft; and said marker is slidable along said shaft and is fixed to a part of said cord.

4. The medical instrument as claimed in claim 1, wherein said transmission unit of said operating mechanism further includes a resilient member disposed on said shaft and connected to said marker, and biasing said marker to move to the non-detectable state.

* * * * *